United States Patent [19]

Ginsburg

[11] Patent Number: 5,011,488
[45] Date of Patent: Apr. 30, 1991

[54] THROMBUS EXTRACTION SYSTEM

[76] Inventor: Robert Ginsburg, 2489 Alpine Rd., Menlo Park, Calif. 94025

[21] Appl. No.: 569,751

[22] Filed: Aug. 20, 1990

Related U.S. Application Data

[63] Continuation of Ser. No. 280,859, Dec. 7, 1988, abandoned.

[51] Int. Cl.$^5$ ............................................. A61M 25/00
[52] U.S. Cl. ................................... 606/159; 604/104
[58] Field of Search ..................... 604/22, 52, 53, 96, 604/97, 98, 99, 100, 101, 102, 103, 104, 159, 264, 281; 606/159, 198, 200

[56] References Cited

U.S. PATENT DOCUMENTS

| | | |
|---|---|---|
| 3,435,826 | 4/1969 | Fogarty . |
| 3,732,858 | 5/1973 | Banko . |
| 4,030,503 | 6/1977 | Clark, III ........................... 606/159 |
| 4,561,439 | 12/1985 | Bishop et al. . |
| 4,573,966 | 3/1986 | Weikl et al. . |
| 4,610,662 | 9/1986 | Weikl et al. . |
| 4,631,052 | 12/1986 | Kensey . |
| 4,636,195 | 1/1987 | Wolinsky . |
| 4,650,466 | 3/1987 | Luther . |
| 4,664,112 | 5/1987 | Kensey et al. . |
| 4,706,671 | 11/1987 | Weinrib . |
| 4,728,319 | 3/1988 | Masch . |
| 4,729,763 | 3/1988 | Henrie . |
| 4,732,154 | 3/1988 | Shiber . |
| 4,734,093 | 3/1988 | Bonello et al. . |
| 4,762,130 | 8/1988 | Fogarty et al. . |
| 4,765,336 | 8/1988 | Fischell et al. ........................ 606/159 |
| 4,794,928 | 1/1989 | Kletschka ............................. 606/194 |
| 4,842,579 | 6/1989 | Shiber .................................... 604/22 |
| 4,886,061 | 12/1989 | Fischell et al. ......................... 604/22 |

OTHER PUBLICATIONS

Starck et al. (1985), Radiology 156: 61–66.

Primary Examiner—C. Fred Rosenbaum
Assistant Examiner—William W. Lewis
Attorney, Agent, or Firm—Townsend and Townsend

[57] ABSTRACT

A vascular catheter system comprises an outer flexible tube, an inner flexible tube disposed in the lumen of the outer flexible tube, and an expandable body mounted at the distal end of the third flexible tube disposed in the lumen of the inner flexible tube. The catheter system is suitable for percutaneous introduction to a blood vessel where the distal end may be located proximate a region of clot or thrombus. By extending the expandable body through the region of clot or thrombus, the obstructing material may be dislodged from the blood vessel wall and drawn toward the open distal end of the inner tube. The inner tube includes an expandable tip which will open to extend substantially across the blood vessel. In this way, the expandable tip will be positioned to collect all of the dislodged clot and thrombus. By withdrawing both the inner tube and the expandable body back into the outer flexible tube, the catheter system may be withdrawn from the patient without appreciable loss of the clot or thrombus.

18 Claims, 3 Drawing Sheets

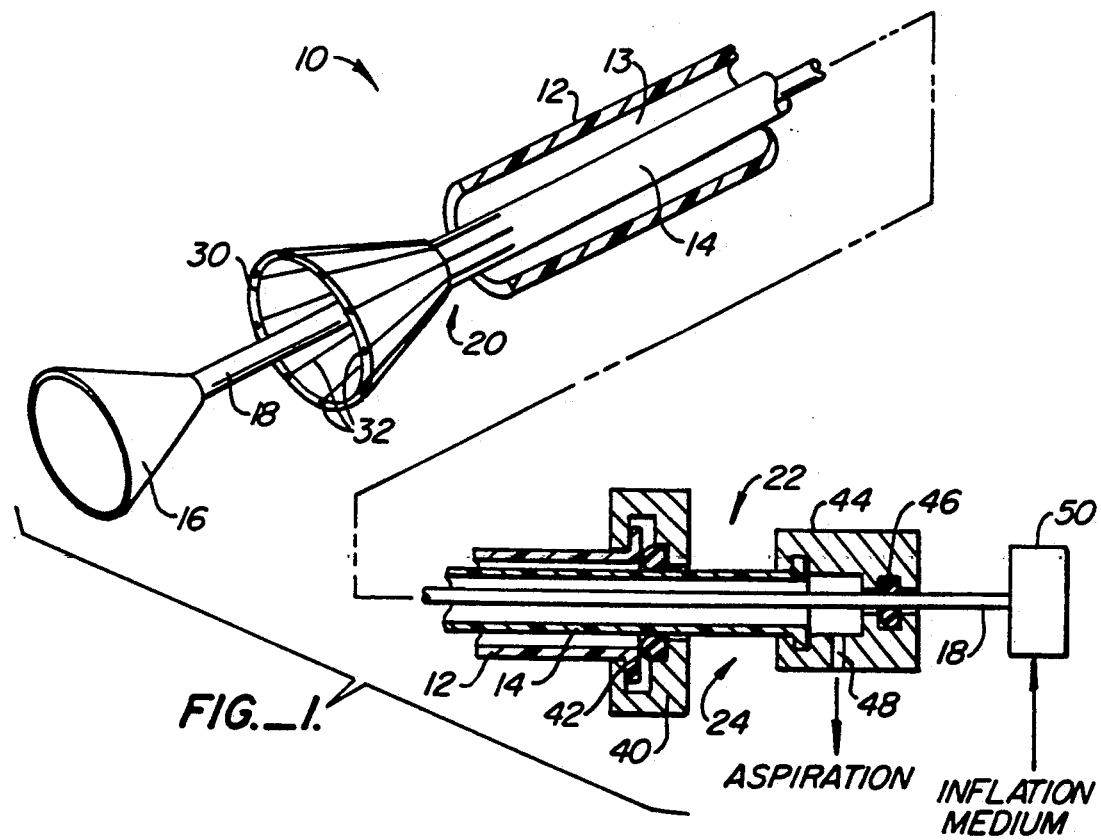
FIG._1.
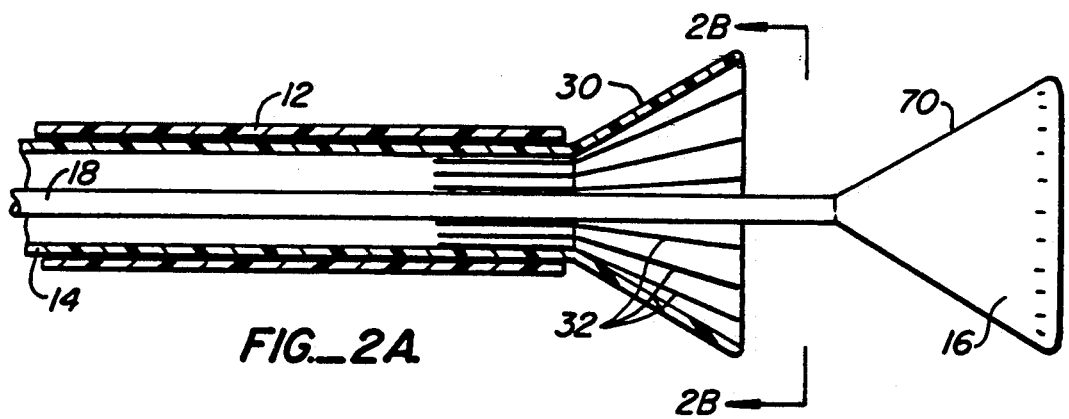
FIG._2A.
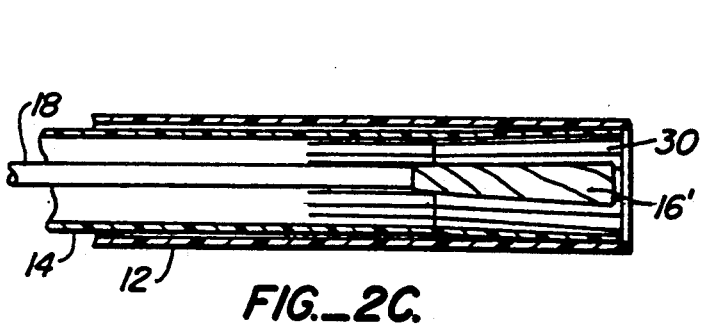
FIG._2C.
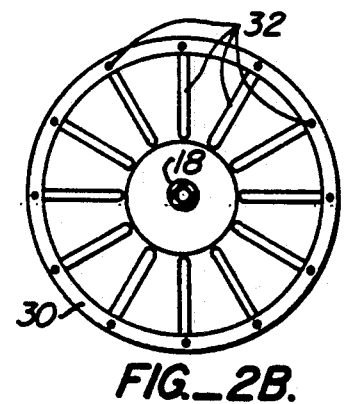
FIG._2B.

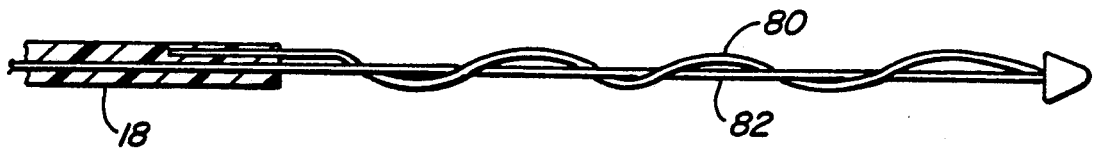
FIG._4A.
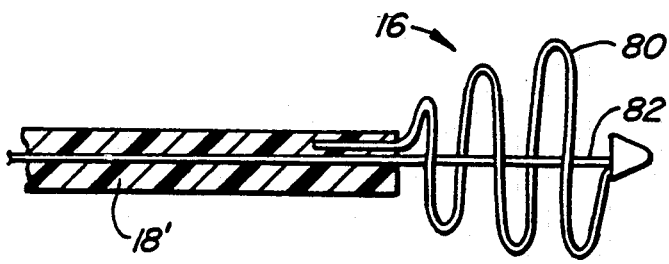
FIG._4B.
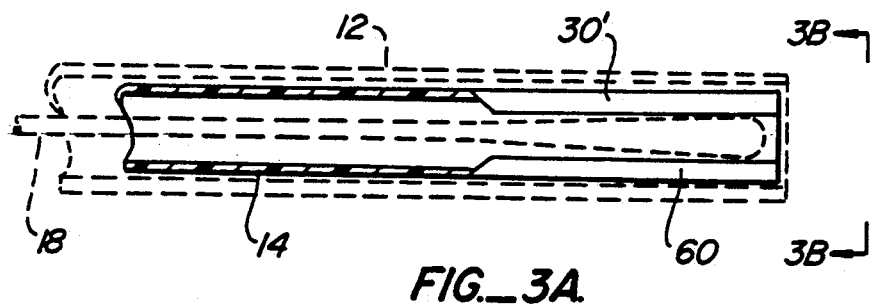
FIG._3A.
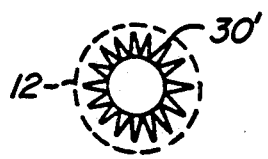
FIG._3B.
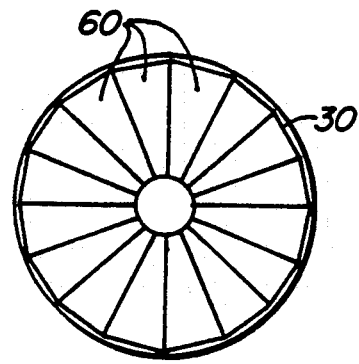
FIG._3C.

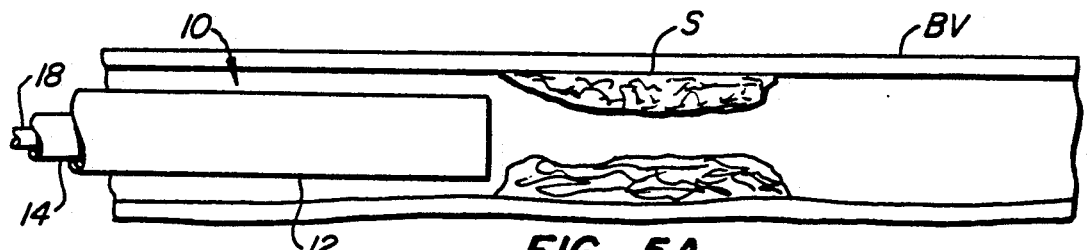
FIG._5A.
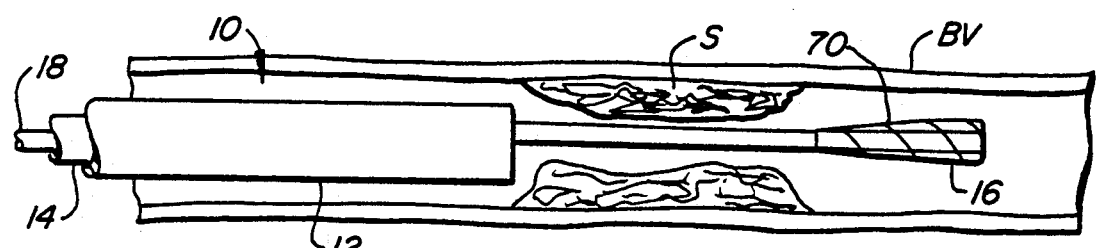
FIG._5B.
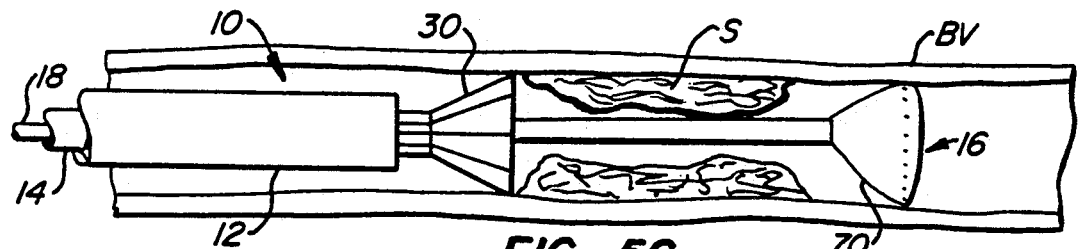
FIG._5C.
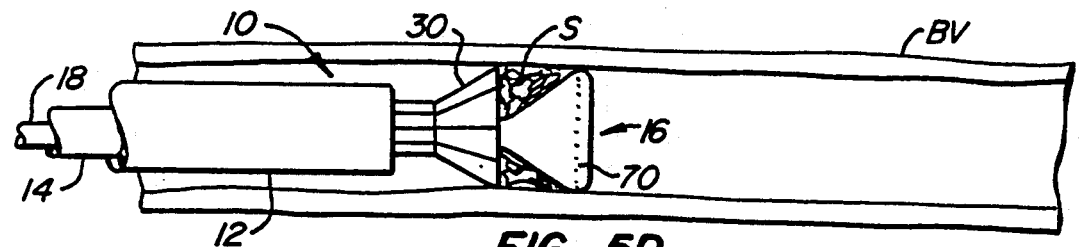
FIG._5D.
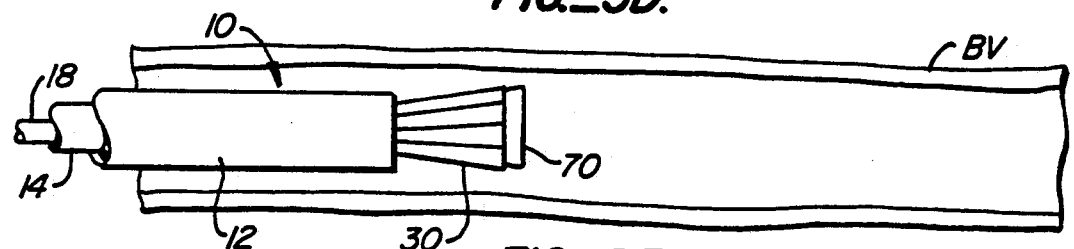
FIG._5E.

THROMBUS EXTRACTION SYSTEM

This is a continuation of application Ser. No. 07/280,859, filed Dec. 7, 1988, now abandoned.

BACKGROUND OF THE INVENTION

1. Field of the Invention

The present invention relates generally to devices and methods for removing thrombus and clot from blood vessels. More particularly, the invention relates to a percutaneous technique where clot and thrombus are dislodged from the blood vessel and collected in the distal end of an intravascular catheter.

Atherosclerosis is a leading cause of death and disability throughout the world. Atherosclerosis is caused by the deposit of fatty substances on the interior wall of a blood vessel, where it is referred to as atheroma or plaque. Such atheromas are found in the peripheral circulatory system as well as the coronary arteries where they can cause severe occlusion of the arterial lumen. Further occluding the blood vessels, clot and thrombus result from platelet aggregation on the irregular surfaces of the lumens caused by the atheroma and plaque. Occluded blood vessels can cause a variety of clinical manifestations, including myocardial infarction (heart attack), angina pectoris, stroke, intermittent claudication, and gangrene. When the blockage of blood flow becomes sufficiently serious, it is necessary to intervene and recanalyze the blood vessel.

Numerous techniques are employed for such recanalization. One of the most common surgical techniques is referred to as embolectomy, where a blood vessel is entered through a surgical incision and a device introduced to the blood vessel for removing the clot and thrombus. Most commonly, a balloon-tipped device (such as the Fogarty catheter) is introduced through a surgical incision and advanced to the location of the occlusion. The balloon is then inflated at a point beyond the clot and used to translate the obstructing material back to the point of incision. The obstructing material can then be removed by the surgeon. While such surgical techniques have been of enormous value, the need to expose a patient to surgery is always traumatic and best avoided when possible.

A variety of percutaneous methods are also utilized for recanalization of blood vessels. The most common of such techniques is referred to as balloon angioplasty, where a balloon-tipped catheter is non-surgically introduced to a blood vessel, typically through an introducing catheter. The balloon-tipped catheter is then advanced to the point of stenosis and inflated in order to dilate the blockage. Balloon angioplasty, thus, does not actually remove stenotic material from the blood vessel, but rather compresses it outwardly in order to increase the available lumen size in the blood vessel. Balloon angioplasty has also been of great value in treating atherosclerosis, but suffers from its own disadvantages. Foremost among these, regions of atheroma and plaque which have been dilated are often subject to rapid restenosis. Even more problematic, the material which has been compressed against the wall of a blood vessel will sometimes dislodge and cause an abrupt closure of the lumen. The latter event can be catastrophic. Thus, balloon angioplasty is indicated only in certain circumstances and is not always successful even when indicated.

Other percutaneous recanalization techniques have also been proposed. Laser angioplasty involves the use of laser energy to oblate stenosis within the blood vessel. Although laser angioplasty has the advantage that the stenotic material is vaporized and not available for restenosis, most laser techniques are limited in their ability to open broad passages within the blood vessels. Indeed, they are frequently used only as a preliminary treatment modality to open a blood vessel sufficiently to allow subsequent balloon angioplasty. Additionally, laser angioplasty, if not properly controlled, can penetrate a blood vessel wall leading to catastrophic results.

A third percutaneous approach has been the use of open-ended catheters to perform aspiration thromboembolectomy. Although relatively safe, the use of negative pressure to collect thrombus is successful only with relatively soft thrombus. In order to improve such aspiration techniques, it has been proposed to use various front-end cutting catheters where a rotating blade is advanced to sever thrombus which is thereafter collected by vacuum in the front end of a catheter. Such improvements enhance the effectiveness of the technique, but increase the danger of vessel penetration by an errant cutting blade.

For these reasons, it would be desirable to provide improved methods for removing clot and thrombus from the interior of blood vessels by percutaneous techniques. In particular, such techniques should provide for effective removal of recalcitrant obstructions with little or no likelihood of traumatizing the blood vessel.

2. Description of the Relevant Art

Embolectomy catheters comprising a flexible catheter body having an inflatable balloon at their distal end are described in U.S. Pat. Nos. 3,435,826; 4,561,439; 4,734,093; and 4,762,130. Such embolectomy catheters are generally surgically introduced so that clot and thrombus may be translated to an incision in the blood vessel from where they can be removed. Embolectomy catheters having wire coils at their distal end are described in U.S. Pat. Nos. 4,706,671, and 4,650,466. The catheter in the '671 patent may be introduced to a blood vessel in a collapsed condition through a needle to remove thrombus. U.S. Pat. Nos. 4,636,195; 4,610,662; and 4,573,966 describe vascular catheters which carry axially spaced-apart balloons at their forward ends. The balloons may be inflated to isolate a region in a blood vessel to allow localized introduction of thrombolytic agents. U.S. Pat. No. 4,631,052, describes a forward cutting catheter which may include a distal balloon (FIG. 9) to prevent release of emboli. Other forward cutting catheters are disclosed in U.S. Pat. Nos. 4,664,112 and 3,732,858. Percutaneous aspiration thromboembolectomy involves the removal of thrombus by aspiration into an open distal end of a catheter. The procedure is described in Starck et al. (1985) Radiology 156:61-66. U.S. Pat. No. 4,729,763, describes a front-end cutting catheter having a tubular auger bit which extends from the distal end of an outer catheter tube. U.S. Pat. No. 4,732,154, describes a front end cutting catheter where a tubular blade is advanced through thrombus over a guidewire having a helical coil thereon. U.S. Pat. No. 4,728,319, describes a front-end cutting catheter which mates with a distally located strainer cup and seal to prevent the release of emboli. U.S. patent application Ser. No. 128,770 (naming applicant herein as the sole inventor) describes a vascular catheter having a strainer at its distal end. The strainer is an expandable structure which utilizes a coaxial sheath for contraction. The strainer is intended to be disposed downstream of various angioplastic techniques to capture released emboli.

SUMMARY OF THE INVENTION

According to the present invention, a novel catheter system is capable of percutaneous removal of clot and thrombus from the interior of a blood vessel. The catheter system comprises an inner flexible catheter tube having an open distal tip. The open tip is expandable so that it can conform to the interior wall of the blood vessel when located proximate the region of stenosis. Conveniently, the inner flexible tube is disposed within the lumen of an outer flexible tube which acts as a sheath capable of containing the expandable tip in a collapsed condition while the inner and outer tubes are being percutaneously introduced to the blood vessel by conventional means. The expandable tip is formed from a resilient material (or is spring-loaded) so that, when extended from the outer tube, it will spring open to conform to the interior wall of the blood vessel. Alternatively, mechanisms may be provided to positively open and close the expandable tip without relying on an outer tube for containment.

The use of the catheter system comprising inner and outer tubes will sometimes be sufficient to remove soft thrombus in a manner similar to transluminal aspiration thromboembolectomy as described above. That is, the tubes may be positioned proximate the region of stenosis, and the inner tube extended forward of the outer tube so that the expandable tip opens and conforms to the blood vessel wall. By then aspirating through the inner flexible tube, relatively soft thrombus may be drawn into the tip and captured by drawing the inner tube back into the outer tube. The expandable tip provides improved collection efficiency for the thrombus material when compared to conventional aspiration thromboembolectomy.

In the case of recalcitrant thrombus, use of the catheter system comprising the inner and outer flexible tubes alone will usually be inadequate. In order to remove such recalcitrant obstructions, the present invention provides an expandable body which may be extended distally from the expandable tip of the inner tube through the region of stenosis. The expandable body may then be expanded and drawn back toward the expanded tip of the inner tube. The expanded tip is thus able to capture the obstructing material which has been dislodged by the translation of the expandable body. Optionally, the inner tube may be aspirated in order to enhance the efficiency of collection. After the material is captured within the expandable tip, the expandable body is drawn fully into the expanded tip. The expanded tip and expandable body are then simultaneously collapsed within the outer tube so that the dislodged material is completely secured within the catheter system. The catheter system may then be removed from the blood vessel and the stenotic material then removed from the catheter. If necessary, the procedure can be repeated in order to remove large amounts of clot and thrombotic material. Conveniently, the expandable body may be an inflatable balloon or an expandable coil.

The present invention is advantageous in that it provides for removal of plaque from a blood vessel without the need for surgical intervention. The device and the method of the present invention provide for improved recanalization of blood vessels when compared to laser angioplasty, and in particular provide for a larger diameter opening through the blood vessel. The present invention is also an improvement over front end cutting catheters in that there is a greatly reduced likelihood of trauma to the blood vessel. Finally, the present invention is an improvement over balloon angioplasty in that there is much less likelihood of abrupt reclosure of the blood vessel.

BRIEF DESCRIPTION OF THE DRAWINGS

FIG. 1 is a perspective view of the catheter system of the present invention shown in partial section.

FIG. 2A is a side elevational view of the distal end of the catheter system of FIG. 1, with the inner catheter and the expandable body shown in their expanded configurations.

FIG. 2B is a sectional view taken along line 2B—2B in FIG. 2A.

FIG. 2C is a view similar to FIG. 2A, except that the inner catheter and expandable body are shown in their collapsed configurations.

FIGS. 3A-3C illustrate an alternative embodiment of the expandable tip of the inner tube of the catheter system of the present invention.

FIGS. 4A and 4B illustrate an alternative embodiment of the expandable body of the present invention.

FIGS. 5A-5E illustrate the method of the present invention.

DESCRIPTION OF THE SPECIFIC EMBODIMENTS

Referring to FIGS. 1 and 2A-2C, a catheter system 10 constructed in accordance with the principles of the present invention comprises an outer flexible tube 12, an inner flexible tube 14 and an expandable body 16 disposed at a distal end of a third flexible member 18. The catheter system 10 extends from distal end 20 to proximal end 22, where a proximal housing 24 is formed.

The outer flexible tube 12 is an elongate catheter tube suitable for percutaneous vascular introduction The length of the tube 12 will vary depending on the intended use. For peripheral arteries, the outer flexible tube 12 will generally have a length in the range from about 30 to 60 cm, while for coronary arteries, the length will generally range from about 100 to 150 cm. The diameter of the catheter will generally vary from about 5 F (French) to about 9 F, more usually varying from about 6 F to 8 F (one French=0.013 inches), with catheters for peripheral arteries generally being larger. The flexible tube 12 may be composed of a wide variety of biologically compatible materials, particularly being formed from elastomers such as silicone rubber, natural rubber, polyvinylchloride, polyurethanes, polyesters, polytetrafluoroethylene, and the like. Frequently, the outer tube 12 may be a composite material having a reinforcement material incorporated therein in order to achieve the desired strength, flexibility, and toughness. The construction of catheter tubes suitable for percutaneous vascular introduction is well described in the patent and medical literature.

The inner flexible tube 14 will be disposed within a central lumen 13 of outer flexible tube 12. The inner flexible tube 14 will be free to reciprocate axially within the outer tube 12, and will usually be free to rotate therein, although the ability to rotate is not a requirement. The outer diameter of the inner tube 14 will be slightly less than the diameter of the central lumen 13 in order to provide the necessary clearance. Typically, clearance in the range from about 0.01 to 0.1 mm will be sufficient, although the precise clearance is not critical. The length of the inner catheter 14 will be greater than that of the outer flexible tube 12, typically being from about 5 to 10 cm greater in length. The greater length is necessary in order to allow the distal end of inner tube 14 to be extended beyond that of the outer tube 12, as will be described in greater detail hereinafter. Suitable materials of construction for the inner tube 14 are generally the same as those described above for the outer tube 12. The inner and outer flexible tubes 14 and 12 may be formed from the same or a different material.

The inner flexible tube 14 terminates at its distal end in an expandable tip 30. The expandable tip 30 will be able to assume an enlarged diameter in comparison to the diameter of the remaining length of the inner flexible tube 14. Specifically, the periphery of the distal end of expandable tip 30 will be able to conform to the inner wall of a blood vessel, as described in more detail hereinafter. The precise structure of the expandable tip 30 is not critical, and it is necessary only that the expandable tip be substantially completely open at its distal end when it is extended from the outer flexible tube 12. In order to achieve such resilient opening, the expandable end 30 may be provided with a plurality of spring elements 32 which, in their unrestrained state, act to open the expandable tip 30 as illustrated in FIGS. 1, 2A and 2B. By retracting the inner tube 14 within the outer tube 12, the expandable tip 30 may be collapsed into the configuration illustrated in FIG. 2C.

The inner tube 14 may be formed by conventional polymer fabrication procedures. For example, an elongate tubular member may be first formed by extrusion of a suitable thermoplastic. The distal tip may then be expanded by heating and subsequent shrink cooling on a mandrel having the desired geometry, i.e., a conical geometry as illustrated in FIGS. 1 and 2A-2C. The spring elements 32 may then be introduced to the distal tip, either integrally or by attaching to the inner surface thereof. The inner tube will then be a single continuous member from the proximate to distal ends. Usually, the thickness of the wall will be less at the expandable tip in order to provide a desired flexibility.

Referring again to FIG. 1, the proximal housing 22 will be constructed to allow relative axial motion of the outer tube 12, inner tube 14, and third flexible member 18. Conveniently, a sealing member 40 may be provided at the proximal end of outer tube 12 in order to seal the open proximal end about the exterior of the inner tube 14. An O-ring 42 will usually be provided in order to afford the necessary sliding seal. Similarly, a seal box 44 having O-ring 46 will be provided in order to seal the open proximal end of inner tube 14 about the third flexible member 18. The sealing box 44 will optionally be provided with a aspiration port 48 so that aspiration may be provided in the inner tube 14, as described in more detail hereinafter. A third sealing box 50 may be provided at the proximal end of the third flexible member 18. In the embodiments of FIGS. 1 and 2A-2C where the expandable body 16 is inflatable, the third sealing box 50 will be provided with a connection for inflation medium. 10 Referring now to FIGS. 3A-3C, an alternative embodiment 30' of the flexible tip on inner tube 14 is illustrated. Flexible tip 30' comprises a plurality of pleats 60 formed from an elastomeric material, where the pleated structure is able to assume a collapsed configuration (as illustrated in FIGS. 3A and 3B) and an expanded or open configuration as illustrated in FIG. 3C. The pleated configuration of FIGS. 3A-3C relies on the inherent resiliency of the elastomeric tip material in order to spring to an open configuration when the tip 30' is extended distally of the outer tube 12.

Referring again to FIGS. 1 and 2A-2C, the expandable body 16 may comprise an inflatable balloon 70 formed at the distal end of the third flexible member 18. In that case, the flexible member 18 will comprise a tube having an inflation lumen running axially therein. The inflatable balloon 70 may be formed from a variety of suitable materials, including polytetrafluoroethylene and polyolefins, such as polyethylene, conveniently formed by heating and cooling over a mandrel having a desired geometry, e.g., conical. Preferably, the conical configuration of balloon 70 will conform to that of the expandable tip 30.

An alternative configuration of the expandable member 16 is illustrated in FIGS. 4A and 4B. There, a wire coil 80 is provided at the end of the third flexible member 18'. The distal end of coil 80 is attached to an extension wire 82 which may be moved between an extended position (FIG. 4A) and a retracted position (FIG. 4B). In the retracted position, the coil assumes an expanded configuration, which can have any desired geometry. As illustrated, the geometry is conical so that the expandable body 16 may be utilized with either of the expandable tips 30 or 30'. In the extended configuration (FIG. 4A), expandable body 16 is collapsed and may be retracted within the inner tube 14 in a manner analogous to the uninflated balloon 16' (FIG. 2C). The construction of coiled embolectomy catheters is described in U.S. Pat. Nos. 4,706,671 and 4,650,466, the disclosures of which are incorporated herein by reference.

Referring now to FIGS. 5A-5E, use of the catheter system 10 of the present invention in clearing a region of thrombus or clot from a blood vessel BV will be described. The catheter system 10 will be percutaneously introduced to the blood vessel BV in its fully retracted configuration as illustrated in FIG. 2C. Non-surgical introduction is accomplished by using an introducing catheter to guide the vascular catheter 10 to the desired blood vessel. Suitable methods for percutaneously introducing the catheter to both peripheral and coronary blood vessels are well known in the art and amply described in the medical and patent literature.

The catheter system 10 will be positioned so that its distal end lies just outside the region of stenosis S. When thus positioned, the inflatable body 16 (illustrated as balloon 70 in FIGS. 5A-5E) is extended distally passing to the other side of the region of stenosis S. This may be accomplished by translating the third flexible element 18 to the right, as illustrated in FIG. 5B. Once the inflatable body 16 is in position, the expandable tip 30 on the inner flexible tube 14 may be extended from the distal end of the outer flexible tube 12, as illustrated in FIG. 5C. The expandable tip 30 will spring open so that its distal periphery contacts the inside wall of the blood vessel BV.

Once the expanded tip 30 is in place, the expandable body 16 may be expanded, e.g., by inflating balloon 70 as illustrated in FIG. 5C. The outer periphery of balloon 70 will also come into contact with the inside wall of the blood vessel BV. By then drawing on the third flexible member 18 to translate the balloon 70 to the left (in reference to FIG. 5C) the thrombus or clot may be dislodged from the blood vessel wall and moved toward the expandable tip 30. Optionally, slight negative pressure may be applied to the interior of inner flexible tube 14 in order to aspirate the dislodged clot or thrombotic material into the expandable tip 30. By the combined action of the balloon 70 and the aspiration, the clot or thrombotic material will be drawn into the inner tube 14, as illustrated in FIG. 5D. By drawing the balloon 70 fully into the expandable tip, as illustrated in FIG. 5E, stenotic material may be captured and sealed within the inner tube 14, and the balloon 70 and inner tube 14 may be simultaneously drawn back into the outer flexible tube 12. In that configuration, the catheter system 10 may be withdrawn from the blood vessel, thus removing the clot or thrombotic material without surgical intervention.

Although the foregoing invention has been described in some detail by way of illustration and example for purposes of clarity of understanding, it will be obvious that certain changes and modifications may be practiced within the scope of the appended claims.

What is claimed is:

1. A catheter system comprising:
an outer flexible tube having proximal and distal ends and a central lumen extending therethrough; and
an inner flexible tube having proximal and distal ends and a central lumen extending therethrough, said inner flexible tube having an open distal tip which assumes an expanded configuration when unconstrained and being reciprocatably disposed in the central lumen of the outer flexible tube, wherein the length of the inner flexible tube is sufficient to extend beyond the proximal end of the central lumen in the outer flexible tube even when the open distal tip extends beyond the distal end of the outer flexible tube, whereby the tip is expended when extended beyond the distal end of the outer tube and collapsed when drawn within the distal end of the outer tube.

2. A catheter system as in claim 1, further comprising: means for drawing clot or thrombus into the tip of the inner flexible tube while said tip is in its expanded configuration.

3. A catheter system comprising:
an outer flexible tube having proximal and distal ends and a central lumen extending therethrough;
an inner flexible tube having proximal and distal ends and a central lumen extending therethrough, said inner flexible tube having an open distal tip which assumes an expanded configuration when unconstrained and being reciprocatably disposed in the central lumen of the outer flexible tube, whereby the tip is expanded when extended beyond the distal end of the outer tube and collapsed when drawn within the distal end of the outer tube; and
an inflatable balloon at a distal end of a flexible inflation tube disposed within the central lumen of the inner flexible tube for drawing clot or thrombus into the tip of the inner flexible tube while said tip is in its expanded configuration.

4. A catheter system as in claim 3, wherein the shape of the inflated balloon is complementary to that of the expanded tip.

5. A catheter system as in claim 4, wherein the complementary shape is substantially conical.

6. A catheter system comprising:
an outer flexible tube having proximal and distal ends and a central lumen extending therethrough;
an inner flexible tube having proximal and distal ends and a central lumen extending therethrough, said inner flexible tube having an open distal tip which assumes an expanded configuration when unconstrained and being reciprocatingly disposed in the central lumen of the outer flexible tube, whereby the tip is expended when extended beyond the distal end of the outer tube and collapsed when drawn within the distal end of the outer tube; and
an expandable coil secured to a distal end of a third flexible tube disposed within the central lumen of the inner flexible tube for drawing clot or thrombus into the tip of the inner flexible tube while said tip is in its expanded configuration.

7. A catheter system comprising:
an inner flexible tube having proximal and distal ends and a central lumen extending therethrough;
means mounted on the distal end of said inner flexible tube for capturing and securing thrombus material therein; and
means comprising an expandable body mounted on a third tube reciprocatably disposed within the central lumen of the inner flexible tube, said expandable body being disposed at the distal end of said inner flexible tube for drawing clot or thrombotic material from a blood vessel into the means for capturing and securing, whereby clot and thrombotic material can be removed by drawing said material into the mans for capturing and securing and withdrawing said inner flexible tube from the blood vessel.

8. A catheter system as in claim 7, wherein the means for capturing and securing clot or thrombus comprises an open tip at the distal end of the flexible tube, said distal tip being convertible between an expanded configuration which captures clot or thrombus and a collapsed configuration which secures the clot or thrombus.

9. A catheter system as in claim 8, wherein the means for capturing and securing clot or thrombus further comprises an outer flexible tube circumscribing the inner flexible tube, whereby the open distal tip is expanded by extending said tip beyond the outer flexible tube and is collapsed by retracting said tip within the outer flexible tube.

10. A catheter system as in claim 7, wherein the expandable body is an inflation balloon.

11. A catheter system comprising:
an inner flexible tube having proximal and distal ends;
an outer flexible tube circumscribing the inner flexible tube having proximal and distal ends;
means mounted on the distal end of said inner flexible tube for capturing and securing thrombus material therein; and
an expandable coil mounted at the distal end of a third flexible tube for drawing clot or thrombus into the means for capturing and securing, said third flexible tube being reciprocatingly disposed within a central lumen of the inner flexible tube.

12. A method for removing clot or thrombus from a blood vessel, said method comprising:
percutaneously introducing a catheter having an open distal end into the blood vessel so that said distal end of the catheter is located proximate the region of clot or thrombus;
extending an expandable body from the distal end of the catheter through the region of clot or thrombus;

expanding the expandable body so that its periphery contacts the inside wall of the blood vessel;

expanding the open distal end of the catheter; and drawing the expandable body in its expanded configuration back to the expanded distal end of the catheter, whereby the thrombus is translated back to said distal end; and capturing the thrombus in the distal end of the catheter.

13. A method as in claim 12, wherein the expandable body is a balloon which is expanded by inflation.

14. A method as in claim 12, wherein the expandable body is a coil which is expanded by compression.

15. A method as in claim 12, further comprising aspirating the catheter while the clot or thrombus is being drawn in by the expandable body.

16. A method as in claim 12, wherein the expandable body is drawn into the expanded distal end of the catheter to complete capture of the clot or thrombus.

17. A method for removing clots or thrombus from a blood vessel, said method comprising:

percutaneously introducing a catheter having an open distal end into the blood vessel so that said distal end of the catheter is located proximate the region of clot or thrombus;

extending an expandable body from the distal end of the catheter through the region of clot or thrombus;

expanding the expandable body so that its periphery contacts the inside wall of the blood vessel;

expanding the distal end of the catheter to facilitate capture of the clot or thrombus;

drawing the expandable body in its expanded configuration back to the expanded distal end of the catheter, whereby said thrombus is translated back to said distal end; and simultaneously collapsing said expandable body and expandable distal end into an outer flexible tube to facilitate removal of the catheter with the clot or thrombus.

18. A method as in claim 17, further comprising aspirating the catheter while the clot or thrombus is being drawn in by the expandable body.

* * * * *